United States Patent
Konomura et al.

(10) Patent No.: US 9,261,693 B2
(45) Date of Patent: Feb. 16, 2016

(54) ENDOSCOPE SYSTEM

(71) Applicant: OLYMPUS CORPORATION, Shibuya-ku, Tokyo (JP)

(72) Inventors: Yutaka Konomura, Tachikawa (JP); Eiichi Kobayashi, Tama (JP); Fumio Hori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 2 days.

(21) Appl. No.: 13/929,564

(22) Filed: Jun. 27, 2013

(65) Prior Publication Data

US 2015/0002841 A1 Jan. 1, 2015

(51) Int. Cl.
| | |
|---|---|
| *G01N 21/00* | (2006.01) |
| *G02B 23/24* | (2006.01) |
| *G01N 21/954* | (2006.01) |
| *F01D 5/12* | (2006.01) |
| *G01M 15/14* | (2006.01) |
| *F01D 21/10* | (2006.01) |
| *F01D 25/28* | (2006.01) |

(52) U.S. Cl.
CPC .............. *G02B 23/2476* (2013.01); *F01D 5/12* (2013.01); *F01D 21/10* (2013.01); *F01D 25/285* (2013.01); *G01M 15/14* (2013.01); *G01N 21/954* (2013.01); *G02B 23/2492* (2013.01)

(58) Field of Classification Search
CPC ........... G82B 23/24; F81D 5/88; F81D 25/88; G81N 21/954; H04N 13/00; A61B 1/008; G06F 15/00; G01J 5/00
USPC ............ 356/241.6, 614–615, 241.1; 600/138, 600/114
See application file for complete search history.

(56) References Cited

U.S. PATENT DOCUMENTS

| | | | |
|---|---|---|---|
| 4,659,195 | A | 4/1987 | D'Amelio et al. |
| 4,784,463 | A | 11/1988 | Miyazaki |
| 5,028,117 | A | 7/1991 | Muhlenkamp-Becker |

(Continued)

FOREIGN PATENT DOCUMENTS

| | | |
|---|---|---|
| DE | 37 07 468 | 9/1987 |
| DE | 19513930 A1 | 9/1996 |

(Continued)

OTHER PUBLICATIONS

Extended European Search Report (EESR) dated Nov. 6, 2013 (in English) issued in counterpart European Application No. 13183761.9.

(Continued)

*Primary Examiner* — Tarifur Chowdhury
*Assistant Examiner* — Isiaka Akanbi
(74) *Attorney, Agent, or Firm* — Holtz, Holtz & Volek PC

(57) ABSTRACT

An endoscope system includes an endoscope having an insertion portion provided with an observation optical system that inspects a plurality of blades that are periodically disposed at a periphery of a rotary shaft of a rotor of an engine, and rotate around the rotary shaft, a guide tube that is introduced into a compressor section, and guides the insertion portion, a first fixing portion that is provided at the guide tube and fixes the guide tube in an inside of the engine, and a second fixing portion that is provided in a position separated by having a predetermined distance from the first fixing portion in the guide tube, and fixes the guide tube with an outer jacketing cover of the engine.

13 Claims, 17 Drawing Sheets

(56) References Cited

U.S. PATENT DOCUMENTS

| | | | |
|---|---|---|---|
| 5,096,292 A * | 3/1992 | Sakamoto et al. | 356/241.4 |
| 5,102,221 A * | 4/1992 | Desgranges et al. | 356/72 |
| 5,155,941 A * | 10/1992 | Takahashi et al. | 451/6 |
| 5,335,061 A * | 8/1994 | Yamamoto et al. | 356/241.1 |
| 5,575,754 A | 11/1996 | Konomura | |
| 7,231,817 B2 * | 6/2007 | Smed | F01D 21/003 73/112.01 |
| 7,518,632 B2 | 4/2009 | Konomura | |
| 8,314,834 B2 | 11/2012 | Konomura | |
| 8,714,038 B2 * | 5/2014 | Moran et al. | 74/55 |
| 2001/0012053 A1 * | 8/2001 | Nakamura | 348/45 |
| 2002/0161284 A1 * | 10/2002 | Tanaka | 600/176 |
| 2004/0176661 A1 * | 9/2004 | Futatsugi | 600/110 |
| 2005/0014996 A1 | 1/2005 | Konomura et al. | |
| 2006/0149126 A1 | 7/2006 | Ertas et al. | |
| 2006/0173243 A1 * | 8/2006 | Watanabe | 600/141 |
| 2007/0171406 A1 | 7/2007 | Stokes | |
| 2008/0262311 A1 * | 10/2008 | Itou | A61B 1/00039 600/152 |
| 2010/0087708 A1 * | 4/2010 | Chen | A61B 1/00105 600/112 |
| 2012/0098940 A1 | 4/2012 | Zombo et al. | |
| 2012/0101769 A1 | 4/2012 | Zombo et al. | |
| 2012/0184814 A1 | 7/2012 | Ebata et al. | |
| 2013/0008233 A1 | 1/2013 | Kosugi et al. | |
| 2013/0135457 A1 | 5/2013 | Kell et al. | |
| 2015/0035968 A1 | 2/2015 | Kobayashi et al. | |
| 2015/0036127 A1 | 2/2015 | Kobayashi et al. | |

FOREIGN PATENT DOCUMENTS

| | | |
|---|---|---|
| EP | 1 811 136 | 7/2007 |
| EP | 2485079 A1 | 8/2012 |
| EP | 2597273 A2 | 5/2013 |
| GB | 2 033 973 | 5/1980 |
| JP | 04267213 A | 9/1992 |
| JP | 2007-163723 A | 6/2007 |
| JP | 2011-039193 A | 2/2011 |
| WO | 2013045108 A1 | 4/2013 |

OTHER PUBLICATIONS

Related U.S. Appl. No. 14/336,660; First Named Inventor: Yutaka Konomura; Title: "Blade Inspection System", filed Jul. 21, 2014.
Related U.S. Appl. No. 14/336,760, First Named Inventor: Yutaka Konomura; Title "Blade Inspection Apparatus"; filed Jul. 21, 2014.

* cited by examiner

ENDOSCOPE SYSTEM

BACKGROUND OF THE INVENTION

1. Field of the Invention

The present invention relates to an endoscope system, and particularly relates to an endoscope system with which inspection of blades of an engine or the like is performed.

2. Description of the Related Art

In recent years, at the time of inspection of the blades of jet engines or the like being performed, endoscope apparatuses have been widely used, in which defect inspection of the blades is performed from inspection images of the blades that are picked up by the insertion portions being inserted into the jet engines.

The art of the conventional endoscope apparatus as above is disclosed in, for example, Japanese Patent Application Laid-Open Publication No. 2007-163723. The Japanese Patent Application Laid-Open Publication No. 2007-163723 discloses the art of a fixing tool that is detachably installed in the vicinity of the access port provided in a jet engine when the insertion portion of the endoscope apparatus is inserted into the jet engine. The fixing tool is installed by two pressing plates being caused to abut on a wall surface of the jet engine, and is fixed to the access port with the insertion portion of the endoscope apparatus being inserted therein.

SUMMARY OF THE INVENTION

An endoscope system according to one aspect of the present invention includes an endoscope having an insertion portion provided with an observation optical system that inspects a plurality of blades that are periodically disposed at a periphery of a rotary shaft of a rotor of an engine, and rotate around the rotary shaft, a guide tube that is introduced into the compressor section, and guides the insertion portion, a first fixing portion that is provided at the guide tube and fixes the guide tube in an inside of the compressor section, and a second fixing portion that is provided in a position separated by having a predetermined distance from the first fixing portion in the guide tube, and fixes the guide tube with an outer jacketing cover of the engine.

According to the present invention, an endoscope system can be provided in which the insertion portion can be fixed to restrict movement of the insertion portion so that the observation distance from a blade of a jet engine or the like is stably kept constant, and which prevents reduction in measurement precision.

The above and other objects, features and advantages of the invention will become more clearly understood from the following description referring to the accompanying drawings.

DETAILED DESCRIPTION OF THE PREFERRED EMBODIMENTS

Hereinafter, embodiments of the present invention will be described with reference to the drawings.

Note that in the following description, the drawings based on embodiments are schematic, attention should be paid to the fact that the relations of the thicknesses and the widths of respective portions, the ratios of thicknesses of the respective portions and the like differ from the actual ones, and among the drawings, parts in which the relations and the ratios of the mutual dimensions differ from one another are also included in some cases.

First Embodiment

First, an endoscope system of a first embodiment of the present invention will be described hereinafter based on the drawings.

Figure 1:
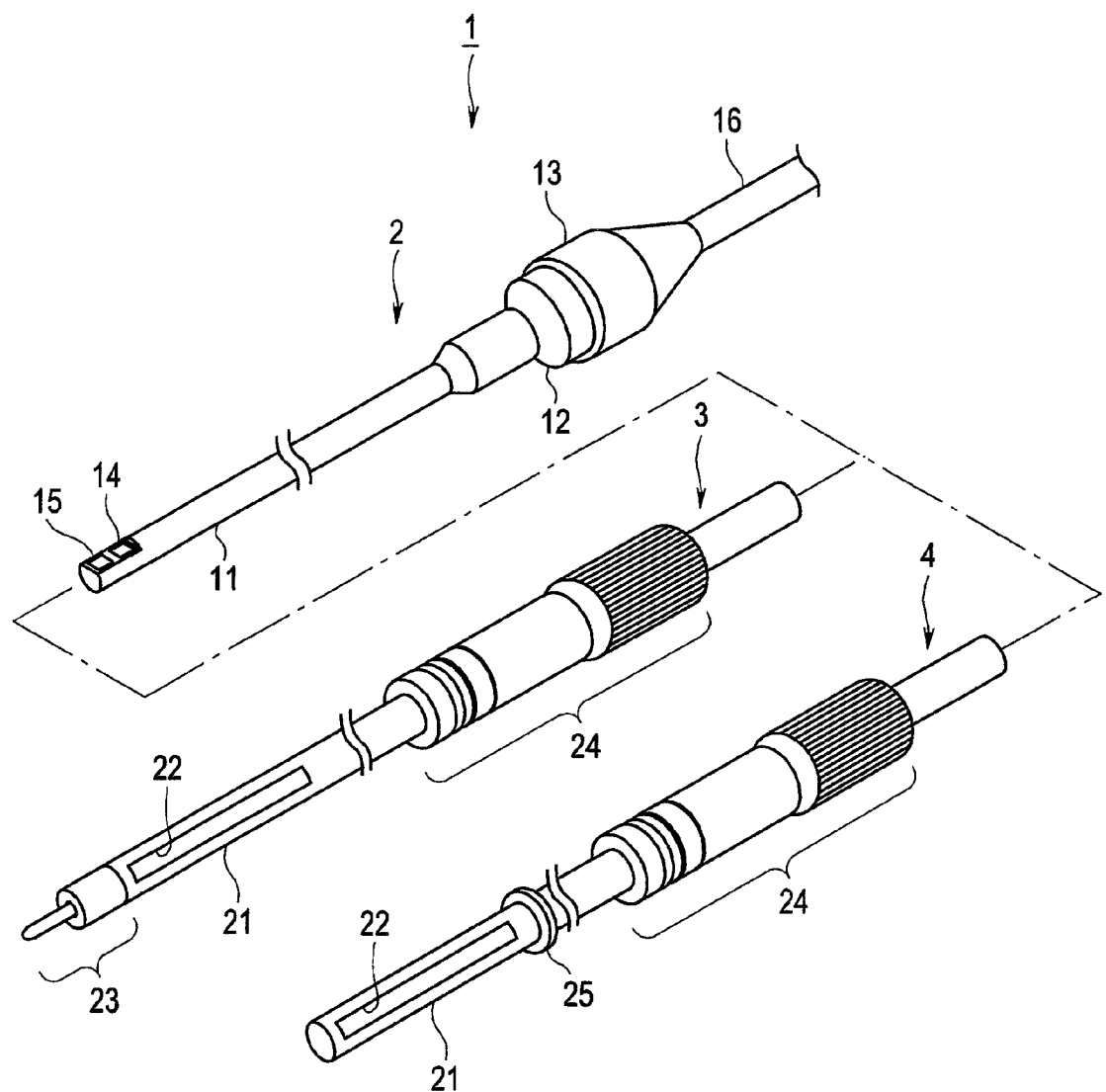
FIG. 1 is a perspective view showing a configuration of an endoscope system according to a first embodiment of the present invention.
Figure 2:
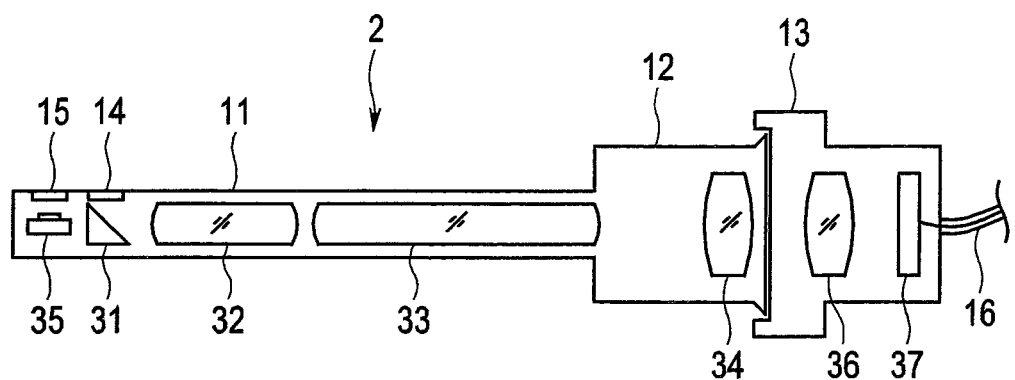
FIG. 2 is a view schematically showing configurations of a borescope and an image pickup apparatus, according to the first embodiment of the present invention.
Figure 3:
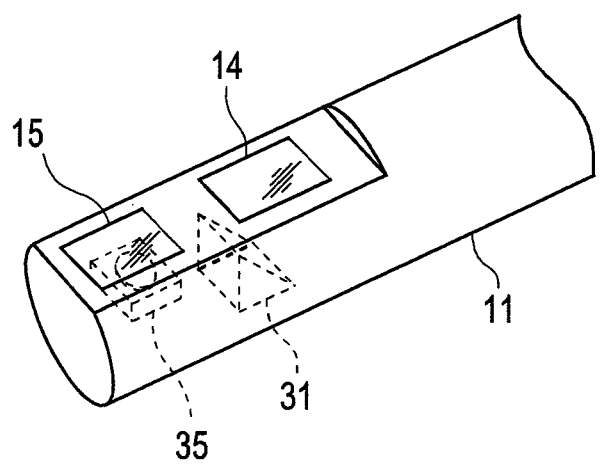
FIG. 3 is a perspective view showing a configuration of a distal end portion of an insertion portion of the borescope, according to the first embodiment of the present invention.
Figure 4:
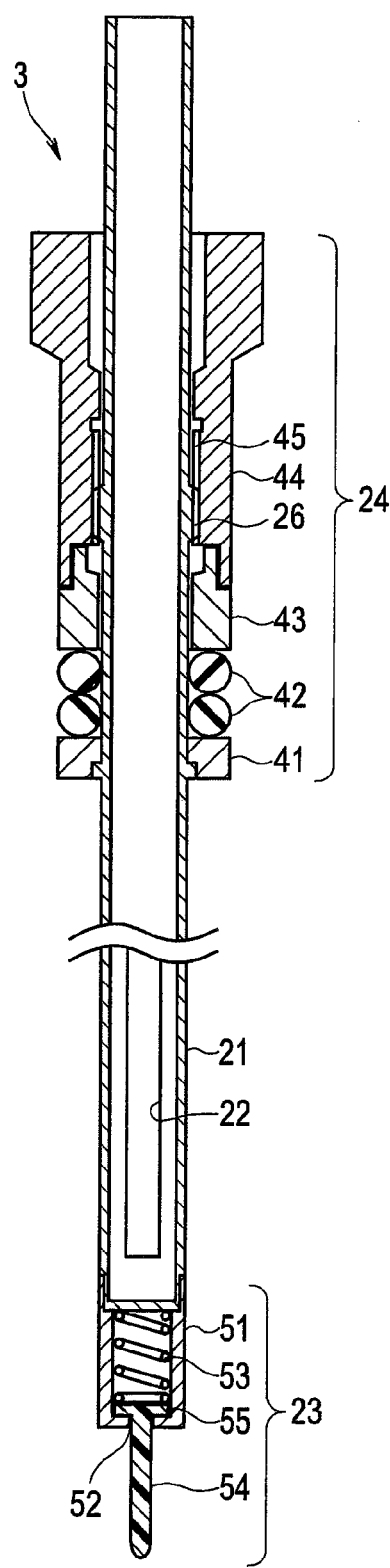
FIG. 4 is a sectional view showing a configuration of an endoscope guide apparatus for a low and medium pressure compressor section, according to the first embodiment of the present invention.
Figure 5:
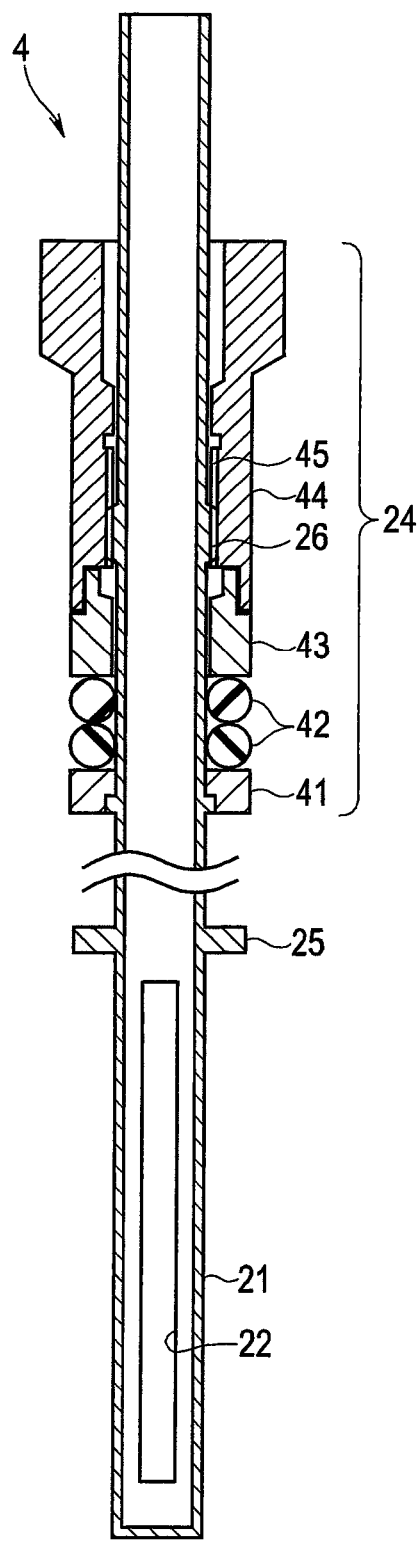
FIG. 5 is a sectional view showing a configuration of an endoscope guide apparatus for a high pressure compressor section, according to the first embodiment of the present invention.
Figure 6:
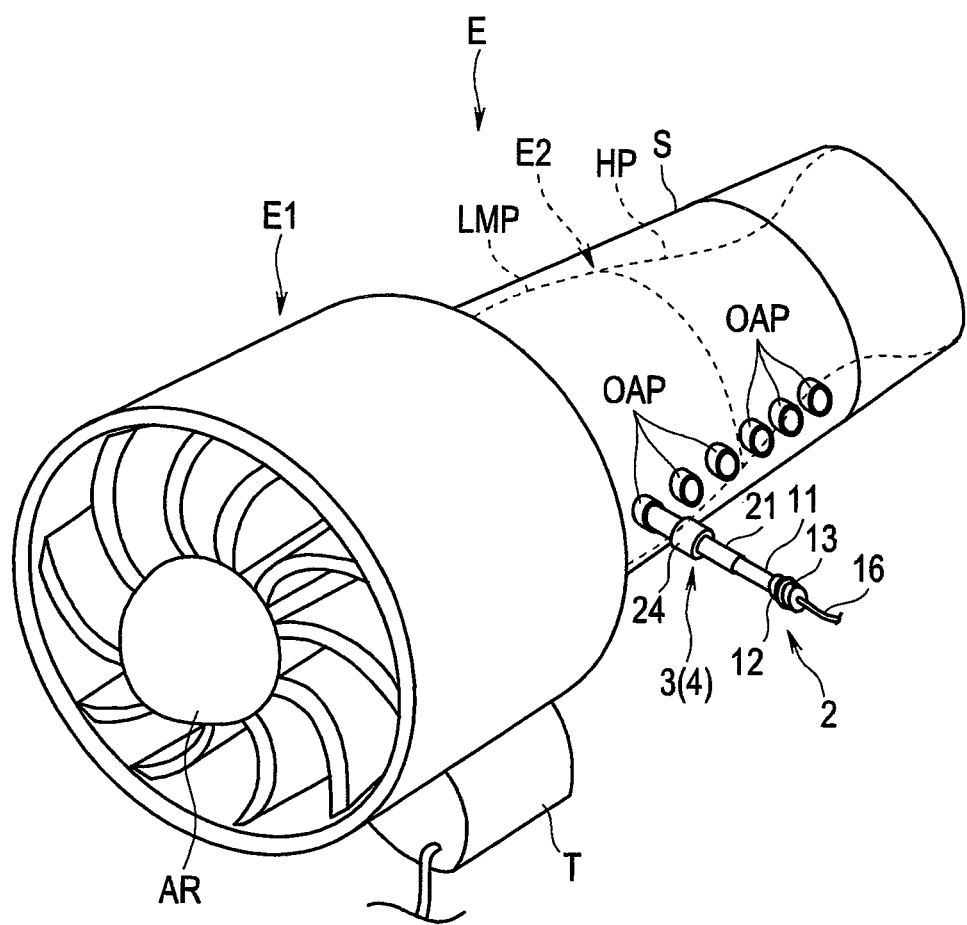
FIG. 6 is a perspective view showing a state of inspection of a jet engine, according to the first embodiment of the present invention.
Figure 7:
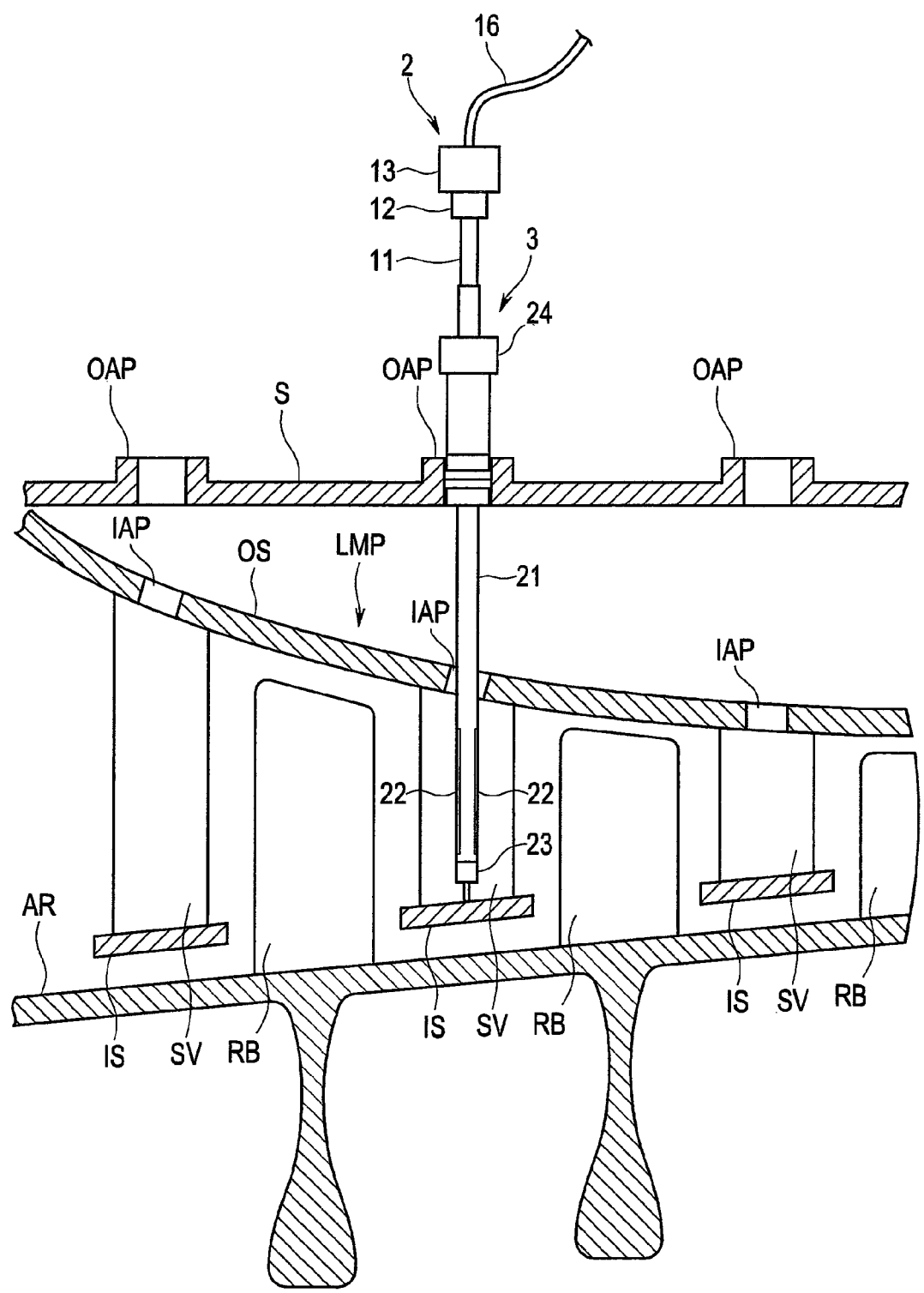
FIG. 7 is a sectional view showing a state of inspection of the low and medium pressure compressor section, according to the first embodiment of the present invention.
Figure 8:
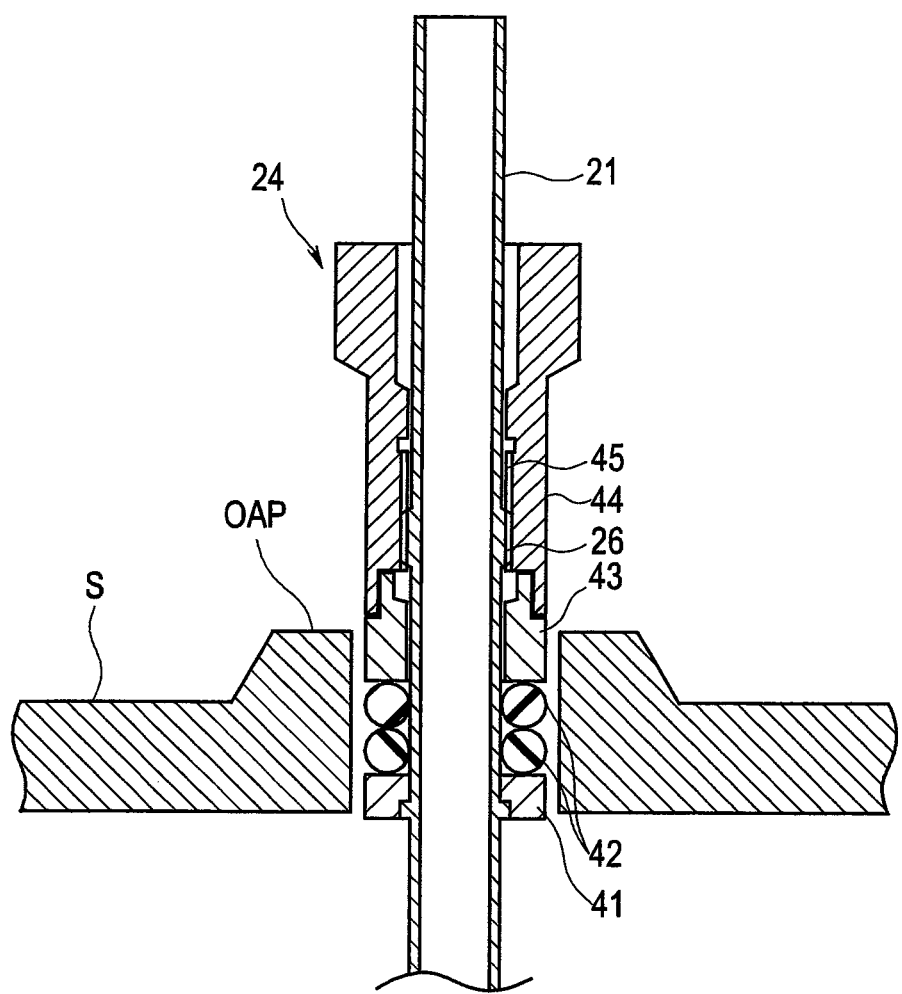
FIG. 8 is a sectional view showing a state in which a second fixing portion is inserted into an external access port, according to the first embodiment of the present invention.
Figure 9:
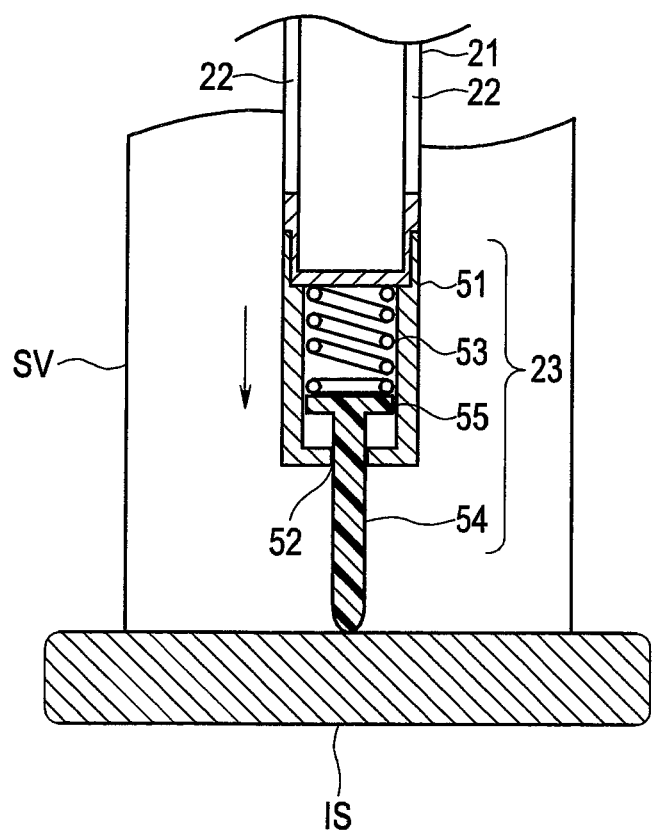
FIG. 9 is a sectional view showing a state in which a first fixing portion of the endoscope guide apparatus for the low and medium pressure compressor abuts on an inner shroud to be fixed, according to the first embodiment of the present invention.
Figure 10:
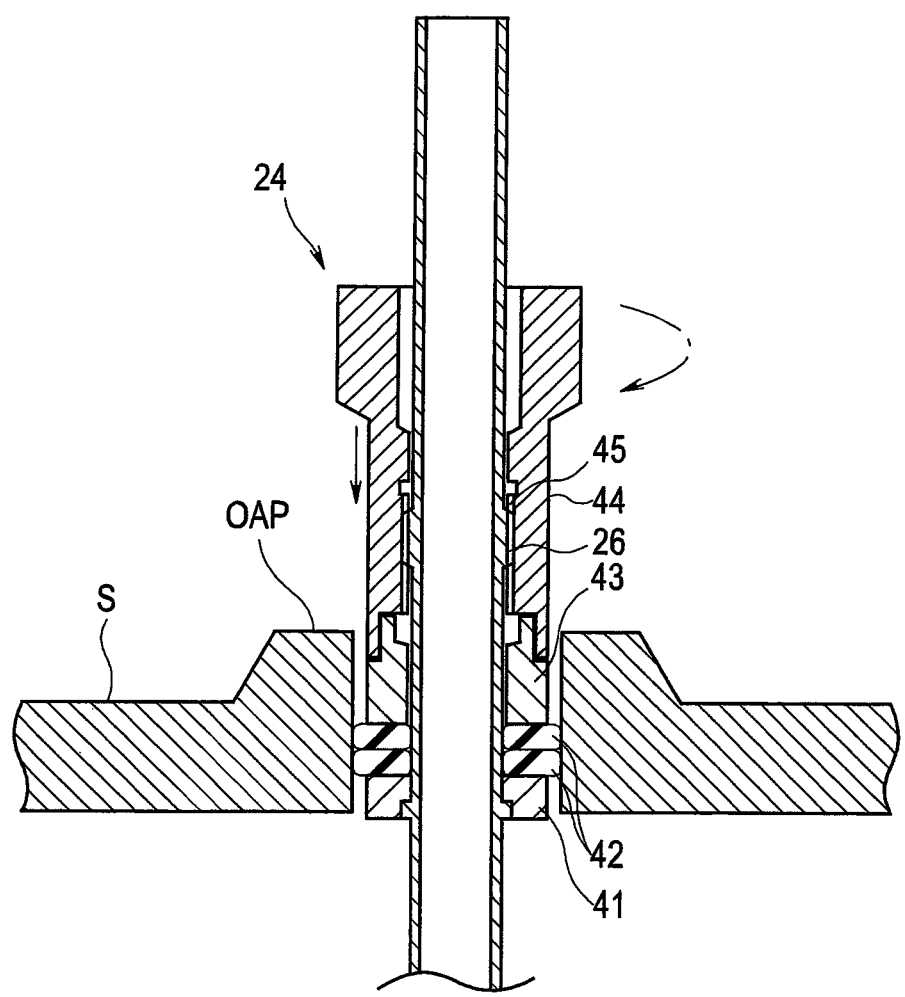
FIG. 10 is a sectional view showing a state in which the second fixing portion is fixed to the external access port, according to the first embodiment of the present invention.
Figure 11:
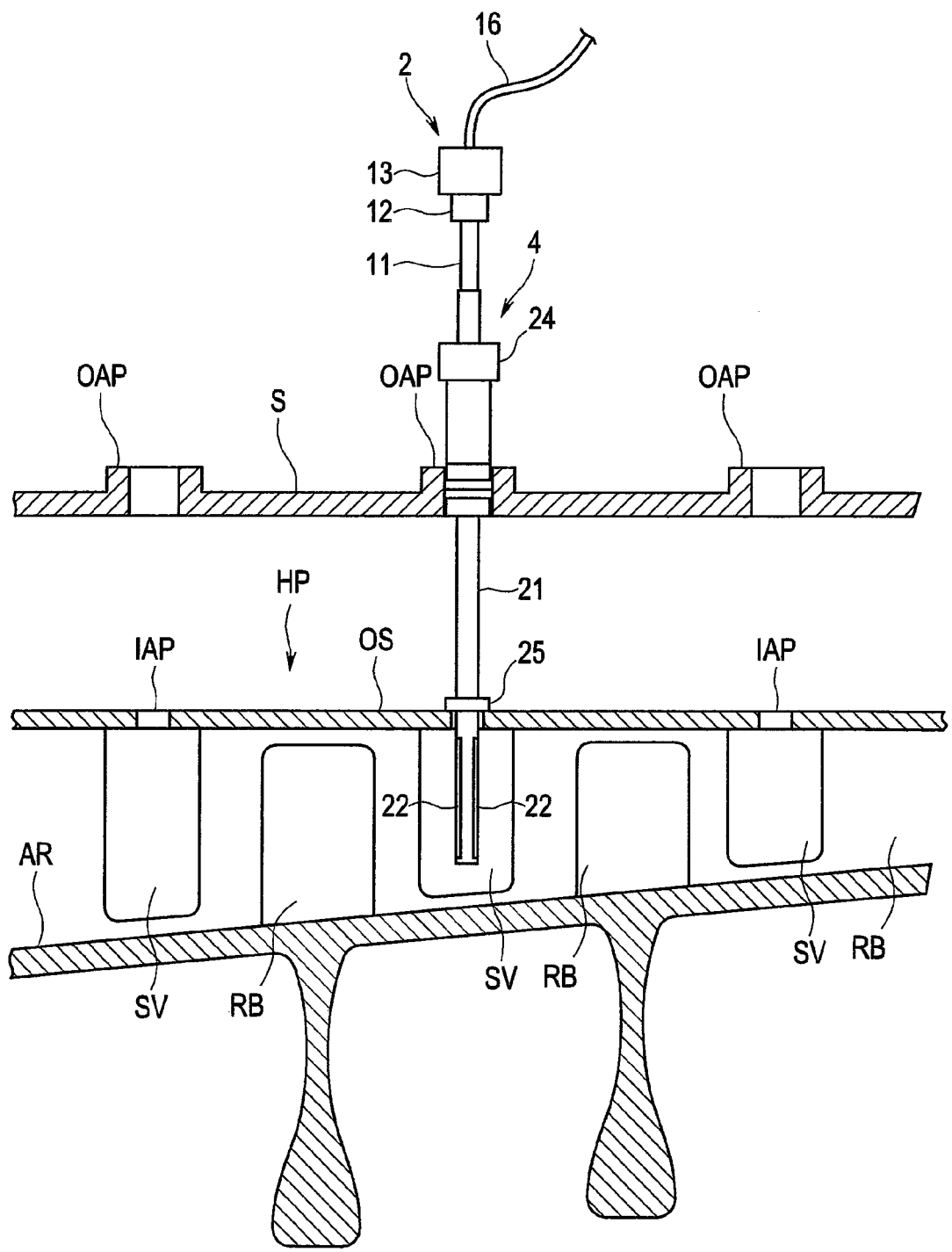
FIG. 11 is a sectional view showing a state of inspection of the high pressure compressor section, according to the first embodiment of the present invention.
Figure 12:
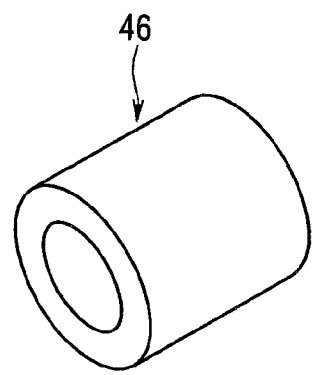
FIG. 12 is a perspective view showing a configuration of a rubber tube provided at a second fixing portion of a modification, according to the first embodiment of the present invention.
Figure 13:
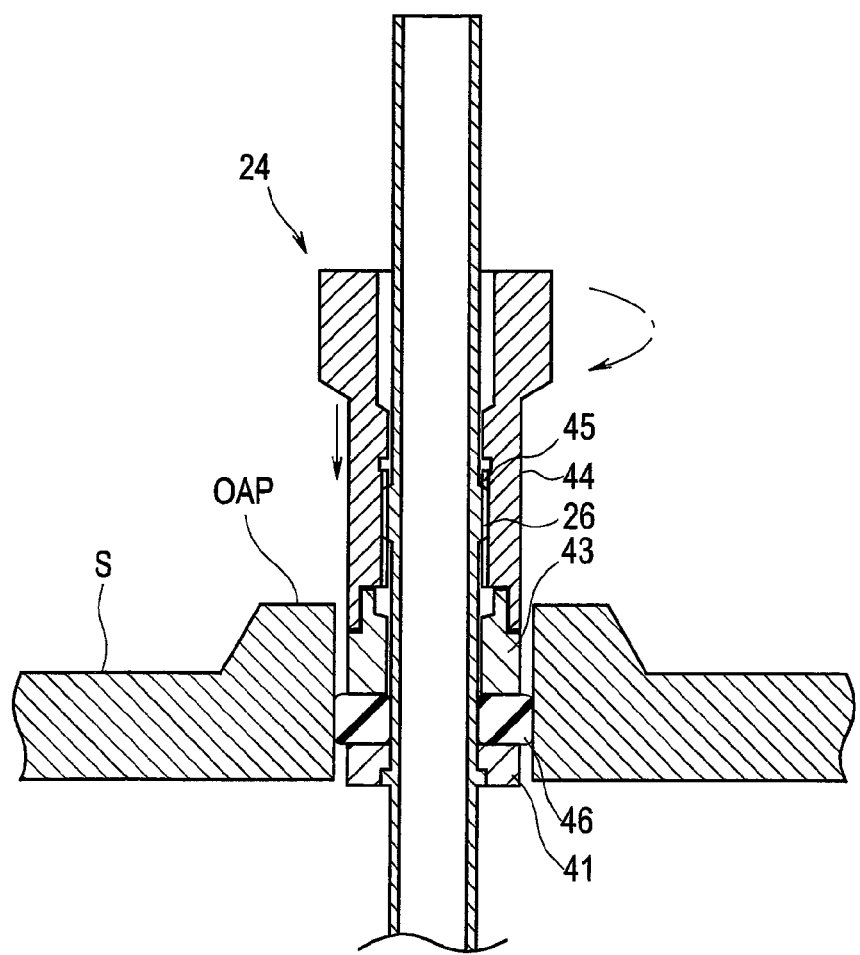
FIG. 13 is a sectional view showing a state in which the second fixing portion of the modification is fixed to the external access port, according to the first embodiment of the present invention.

FIG. 1 to FIG. 13 relate to the first embodiment of the present invention. FIG. 1 is a perspective view showing an entire configuration of the endoscope system. FIG. 2 is a view schematically showing configurations of a borescope and an image pickup apparatus. FIG. 3 is a perspective view showing a configuration of a distal end portion of an insertion portion of the borescope. FIG. 4 is a sectional view showing a configuration of an endoscope guide apparatus for a low and medium pressure compressor section. FIG. 5 is a sectional view showing a configuration of an endoscope guide apparatus for a high pressure compressor section. FIG. 6 is a perspective view showing a state of inspection of a jet engine. FIG. 7 is a sectional view showing a state of inspection of the low and medium pressure compressor section. FIG. 8 is a sectional view showing a state in which a second fixing portion is inserted into an external access port. FIG. 9 is a sectional view showing a state in which a first fixing portion of the endoscope guide apparatus for the low and medium compressor section abuts on an inner shroud to be fixed. FIG. 10 is a sectional view showing a state in which the second fixing portion is fixed to the external access port. FIG. 11 is a sectional view showing a state of inspection of the high pressure compressor section. FIG. 12 is a perspective view showing a configuration of a rubber tube provided at a second fixing portion of a modification. FIG. 13 is a sectional view showing a state in which the second fixing portion of the modification is fixed to the external access port.

As shown in FIG. 1, an endoscope system 1 of the present embodiment is configured by mainly having a borescope 2 as an endoscope, and an endoscope guide apparatus 3 for a low and medium pressure compressor section (hereinafter, called a first endoscope guide apparatus) and an endoscope guide apparatus 4 for a high pressure compressor section (hereinafter, called a second endoscope guide apparatus) that are inserted into compressor sections of a jet engine or the like as objects to be examined that will be described later.

The borescope 2 in this case is a side-view type endoscope, and has a cylindrical insertion portion 11 provided with an observation window 14 and an illuminating window 15 at a side portion of a distal end portion, and an eyepiece portion 12 placed at a proximal end portion of the insertion portion 11. Note that in this case, a detachable image pickup apparatus 13 is fitted to the eyepiece portion 12 of the borescope 2.

In an inside of the borescope 2, observation means and illumination means are disposed. More specifically, as shown in FIG. 2 and FIG. 3, in the insertion portion 11 of the borescope 2, a mirror 31, an objective optical system 32 and a relay optical system 33 as an observation optical system, and an LED 35 as the illumination means in this case are disposed. Note that the observation window 14 and the illuminating window 15 are provided with transparent members of glass or the like.

The mirror 31 is disposed in a distal end portion of the insertion portion 11. The mirror 31 is an optical member that guides light incident on the insertion portion 11 from a side surface of the borescope 2 to a direction of the eyepiece portion 12. The objective optical system 32 is disposed at a distal end side of the borescope 2 in the insertion portion 11, and is an optical member for forming a real image of an object.

The LED 35 is an illuminating light source that emits illuminating light to the object, is connected to a wiring cable not illustrated that is placed in the insertion portion 11, and is supplied with drive power by the wiring cable.

Note that the power that drives the LED 35 may be configured to be supplied from an outside, or a configuration in which a battery for power supply is provided in the borescope 2 may be adopted. Further, the illumination means is not limited to the LED 35, but may be configured to transmit the illuminating light from an external light source by a light guide bundle.

The eyepiece portion 12 of the borescope 2 is provided with an eyepiece optical system 34 that makes an image transmitted by the relay optical system 33 visible. In the image pickup apparatus 13 as a camera that is fitted to the eyepiece portion 12, an image pickup optical system 36 and a solid image pickup device 37 are disposed.

The image pickup optical system 36 forms an image of an object image that is made visible on the eyepiece portion 12 of the borescope 2. The solid image pickup device 37 picks up an image of the object image formed by the image pickup optical system 36.

An image pickup signal that is a video signal that is photoelectrically converted in the solid image pickup device 37 is outputted to a personal computer (PC) not illustrated via a signal cable 16. Note that the image pickup signal from the solid image pickup device 37 may be configured to be outputted to a video processor or the like via the signal cable 16.

The configurations of the borescope 2 and the image pickup apparatus 13 described above are known, and therefore, the detailed description of the other components will be omitted.

Next, the first endoscope guide apparatus 3 and the second endoscope guide apparatus 4 will be described hereinafter.

As shown in FIG. 4, the first endoscope guide apparatus 3 is configured by mainly having an insertion portion guide tube 21, a first fixing portion 23 and a second fixing portion 24.

The insertion portion guide tube 21 is a rigid tube of a metal or the like with a distal end side closed, in which the insertion portion 11 of the borescope 2 is insertable and removable. The first fixing portion 23 is connectively provided at a distal end of the insertion portion guide tube 21. The second fixing portion 24 is provided at a midpoint on a proximal end side of the insertion portion guide tube 21. That is, the first fixing portion 23 and the second fixing portion 24 are provided at positions that are separated by having a predetermined distance from each other, of the insertion portion guide tube 21.

In the insertion portion guide tube 21, an observation opening portion 22 as a long hole along a longitudinal direction is formed at a side circumferential portion from the distal end side to a midpoint. The observation opening portion 22 is a window portion for enabling observation of the object by the borescope 2 in a state in which the insertion portion 11 of the borescope 2 is inserted in the insertion portion guide tube 21.

That is, in the borescope 2, the observation window 14 and the illuminating window 15 are exposed from the observation opening portion 22, and thereby observation of an object by the borescope 2 is enabled without visibility being impaired by the insertion portion guide tube 21.

The first fixing portion 23 is configured by mainly having a case body 51, a coil spring 53 and a rod body 54. The case body 51 is in a substantially cylindrical shape having a hole portion 52 at a distal end. The case body 51 is fixed to the distal end of the insertion portion guide tube 21 by being screwed, press-fitted or the like.

The rod body 54 has a flange 55 at one end, and is formed from a resin, a rigid rubber, a metal or the like. Further, the rod body 54 is disposed to be inserted through the hole portion 52 of the case body 51 with the flange 55 housed in the case body 51.

The coil spring 53 is housed in the substantially cylindrical case body 51 so as to abut on a distal end face of the insertion portion guide tube 21 and the flange 55.

The rod body 54 of the first fixing portion 23 is in a state in which the rod body 54 is protruded from the hole portion 52 of the case body 51, and is urged to a distal end side by an urging force of the coil spring 53. That is, the coil spring 53 configures an urging member that is placed in the case body 51 and urges the rod body 54 to the distal end side.

The second fixing portion 24 is configured by mainly having a fixed ring member 41, two O-rings 42 in this case, a moving cylinder body 43, and a rotating handle 44. The fixed ring member 41 is fixed to a midpoint outer circumferential portion of the insertion portion guide tube 21 by fitting, bonding or the like.

The two O-rings 42 are externally fitted on the insertion portion guide tube 21, and is provided in parallel by being connected to a proximal end side of the fixed ring member 41. The moving cylinder body 43 is disposed at a proximal end side of the O-ring 42 by being externally fitted rotatably on the insertion portion guide tube 21.

The rotating handle 44 is a substantially cylinder body, and is disposed by being externally fitted rotatably on the insertion portion guide tube 21 so that a distal end side abuts on the moving cylinder body 43. A female screw portion 45 is formed on an inner circumferential face of the rotating handle 44.

The female screw portion 45 is meshed with a male screw portion 26 provided on an outer circumferential portion of the insertion portion guide tube 21. That is, the rotating handle 44 moves to advance and retract along the longitudinal direction of the insertion portion guide tube 21 by a screw feeding mechanism by the female screw portion 45 and the male screw portion 26 by rotating in a predetermined direction around a longitudinal axis of the insertion portion guide tube 21.

Note that when the rotating handle 44 is rotationally operated and moves to the distal end side, the rotating handle 44 presses the moving cylinder body 43 to the distal end side. Thereupon, a separation distance of the moving cylinder body 43 and the fixed ring member 41 is reduced. Thereby, the two O-rings 42 that are provided between the moving cylinder body 43 and the fixed ring member 41 are configured to be crushed and protrude in an outside diameter direction.

As shown in FIG. 5, the second endoscope guide apparatus 4 is configured to have the insertion portion guide tube 21 and the second fixing portion 24 without being provided with the first fixing portion 23, unlike the first endoscope guide apparatus 3.

Further, the insertion portion guide tube 21 of the second endoscope guide apparatus 4 is provided with a fixing flange 25 as a first fixing portion in a vicinity of the observation opening portion 22, at a proximal end side from the observation opening portion 22, in addition to the configuration of the insertion portion guide tube 21 of the first endoscope guide apparatus 3. The fixing flange 25 is also provided at a position separated by having a predetermined distance with respect to the second fixing portion 24 of the insertion portion guide tube 21.

Note that a configuration of the second fixing portion 24 of the second endoscope guide apparatus 4 is the same configuration as the second fixing portion 24 of the first endoscope guide apparatus 3, and therefore, the detailed description of the configuration will be omitted.

The endoscope system 1 of the present embodiment that is configured as above has the first endoscope guide apparatus 3 or the second endoscope guide apparatus 4 inserted into a jet engine (hereinafter, simply called an engine) E that is an object to be examined, as shown in FIG. 6. Subsequently, the insertion portion 11 of the borescope 2 is inserted into the insertion portion guide tube 21, and endoscope inspection of a plurality of blades (hereinafter, called rotor blades or stator vanes) in an inside of the engine E that is an object to be inspected.

Here, the engine E will be briefly described.

As shown in FIG. 6, the engine E has an intake section E1, a compressor section E2, a combustion section and an exhaust section (both are not illustrated in detail), from an intake side to an exhaust side.

The compressor section E2 is covered with a cylindrical skin S to be an external jacketing cover. The compressor section E2 is an axial flow compressor, has a plurality of stages, and in an inside thereof, has a low and medium pressure compressor portion LMP and a high pressure compressor portion HP disposed in sequence from the intake side to the exhaust side.

The skin S is provided with a plurality of, six in this case, external access ports OAP that are to be introduction ports for the first endoscope guide apparatus 3 or the second endoscope guide apparatus 4. In hole portions of the external access ports OAP, the insertion portion guide tube 21 of the first endoscope guide apparatus 3 or the second endoscope guide apparatus 4 is inserted. The borescope 2 is inserted into an inside of the compressor section E2 via the insertion portion guide tube 21.

In this manner, the endoscope system 1 inspects a plurality of rotor blades RB or stator vanes SV (see FIG. 7) in the compressor section E2 of the engine E by the first endoscope guide apparatus 3 or the second endoscope guide apparatus 4 and the borescope 2. Note that in a state in which the first fixing portion 24 and the second fixing portion 23 are fixed, the observation opening portion 22 is disposed in a position in which the borescope 2 can observe the a distal end side of the stator blade SV or a proximal end side of the rotor blade RB.

Incidentally, endoscope inspection is performed by a turning tool T being connected to the engine E. The turning tool T is an apparatus for rotating a rotary shaft AR, includes a motor and a gear box, and can rotate the rotary shaft AR via a shaft (not illustrated).

At a time of endoscope inspection, while a plurality of rotor blades that will be described later are rotated around the rotary shaft AR with use of the turning tool T, the plurality of rotor blades provided at the rotary shaft AR are photographed and the endoscope inspection is performed, by the borescope 2 that is inserted in the inside of the compressor section E2.

Here, an operation of fixing by inserting the first endoscope guide apparatus 3 or the second endoscope guide apparatus 4 into the compressor section E2 of the engine E at the time of endoscope inspection performed by the endoscope system 1 of the present embodiment will be described.

First, in endoscope inspection of the low and medium pressure compressor portion LMP of the compressor section E2, the first endoscope guide apparatus 3 is used as shown in FIG. 7.

The insertion portion guide tube 21 of the first endoscope guide apparatus 3 is introduced from the external access port OAP at an introduction port provided in the skin S of the engine E. Further, the insertion portion guide tube 21 is inserted into a hole portion of an internal access port IAP that is an introduction port formed in an outer shroud OS that is an engine case that fixes the stator vanes SV.

In this manner, the insertion portion guide tube 21 of the first endoscope guide apparatus 3 is introduced into the low and medium pressure compressor section LMP of the compressor section E2. At this time, in the first fixing portion 23 that is placed at the distal end of the insertion portion guide tube 21, the rod body 54 abuts on and is butted to an inner shroud IS that is a member of an engine case that fixes the stator vane SV.

From the above state, the insertion portion guide tube 21 is pushed into a position in which the two O-rings 42 of the second fixing portion 24 face a hole portion inner circumferential wall in a thickness direction of the external access port OAP of the skin S, as shown in FIG. 8.

Thereby, the rod body 54 is brought into a state in which the rod body 54 is pushed into the case body 51 against the urging force of the coil spring 53 that abuts on the flange 55, as shown in FIG. 9. That is, the rod body 54 is brought into a state in which the rod body 54 presses a surface of the inner shroud IS of the stator by the urging force of the coil spring 53.

In this manner, the insertion portion guide tube 21 is fixed in a state in which the insertion portion guide tube 21 presses the surface of the inner shroud IS of the stator by the rod body 54 of the first fixing portion 23.

From the state, in the second fixing portion 24, the rotating handle 44 is rotated in a direction to fasten the two O-rings 42. Thereby, the rotating handle 44 moves to the distal end side, and presses the moving cylinder body 43, and as shown in FIG. 10, the two O-rings 42 that are provided between the moving cylinder body 43 and the fixed ring member 41 are crushed, and protrude in an outside diameter direction.

Thus, the insertion portion guide tube 21 is fixed to the external access port OAP by the two O-rings 42 protruded in the outside diameter direction of the second fixing portion 24 contact the hole portion inner circumferential wall in the thickness direction of the external access port OAP of the skin S in such a manner as to press the hole portion inner circumferential wall.

Subsequently, the insertion portion 11 of the borescope 2 is inserted into the insertion portion guide tube 21 of the first endoscope guide apparatus 3, and endoscope inspection of the stator vane SV or the rotor blade RB in the low and medium pressure compressor section LMP is performed.

Meanwhile, as shown in FIG. 11, in endoscope inspection of the high pressure compressor section HP of the compressor section E2, the second endoscope guide apparatus 4 is used. That is, in the high pressure compressor section HP, by the borescope 2 that is guided by the insertion portion guide tube 21 of the second endoscope guide apparatus 4, the rotor blade RB or the stator vane SV is photographed, and endoscope inspection is performed.

In this case, the insertion portion guide tube 21 of the second endoscope guide apparatus 4 is also introduced from the external access port OAP of the introduction port that is provided in the skin S of the engine E. Further, the insertion portion guide tube 21 is inserted into a hole portion of the internal access port IAP of the introduction port that is formed in the outer shroud OS of the engine case that fixes the stator vane SV, and is introduced into the high pressure compressor section HP.

Incidentally, in the high pressure compressor section HP, the stator vanes SV are fixed to only the outer shroud OS, and the inner shroud IS that fixes the stator vanes SV is not sometimes provided. Accordingly, the fixing flange 25 that is placed at the midpoint of the insertion portion guide tube 21 is butted to the surface of the outer shroud OS as the member located around the hole portion of the internal access port IAP.

In this manner, the second endoscope guide apparatus 4 is fixed in a state in which the fixing flange 25 as the first fixing portion abuts on the surface of the outer shroud OS.

Note that the second fixing portion 24 of the second endoscope guide apparatus 4 is fixed to the external access port OAP by the rotating handle 44 being rotated in a direction to fasten the two O-rings 42, and the two O-rings 42 protruded in the outside diameter direction contacting the hole portion inner circumferential wall in the thickness direction of the external access port OAP of the skin S in such a manner as to press the hole portion inner circumferential wall.

Subsequently, the insertion portion 11 of the borescope 2 is inserted into the insertion portion guide tube 21 of the second endoscope guide apparatus 4, and endoscope inspection of the stator vane SV or the rotor blade RB in the high pressure compressor section HP is performed. Note that when the first fixing portion 24 and the second fixing portion 25 are fixed, the observation opening portion 22 is disposed in a position in which the borescope 2 can observe the distal end side of the stator blade SV or the proximal end side of the rotor blade RB.

As above, the endoscope system 1 of the present embodiment is configured so that an axis of the insertion portion guide tube 21 does not move by fixing the insertion portion guide tube 21 of the first endoscope guide apparatus 3 or the second endoscope guide apparatus 4 that is introduced into the compressor section E2 of the engine E at two spots that are the first fixing portion 23 or the fixing flange 25 as the first fixing portion, and the second fixing portion 24.

Note that the insertion portion guide tube 21 of the first endoscope guide apparatus 3 or the second endoscope guide apparatus 4 has a length set in accordance with the respective access ports of the compressor section E2.

As described above, the endoscope system 1 of the present embodiment can make the axis of the insertion portion guide tube 21 immovable without swinging, because the insertion portion guide tube 21 of the first endoscope guide apparatus 3 or the second endoscope guide apparatus 4 that guides the insertion portion 11 of the borescope 2 is fixed at the two spots separated by the predetermined distance in the axial direction.

Therefore, the endoscope system 1 can guide the insertion portion 11 of the borescope 2 in the state in which the insertion portion guide tube 21 of the first endoscope guide apparatus 3 or the second endoscope guide apparatus 4 is fixed so that the observation distance from the stator vane SV or the rotor blade RB that is the blade of the engine E is stably kept constant, and therefore, can prevent reduction in measurement precision by the borescope 2.

(Modification)

Note that the second fixing portion 24 may use a cylindrical rubber tube 46 as shown in FIG. 12, instead of the two O-rings 42.

When description is made in detail, in the second fixing portion 24 of the present modification, when the rotating handle 44 is rotationally operated and moves to the distal end side, the rotating handle 44 presses the moving cylinder body 43 to the distal end side, and the rubber tube 46 that is provided between the moving cylinder body 43 and the fixed ring member 41 is crushed and protrudes in an outside diameter direction.

That is, when the rotating handle 44 is rotated in the direction to fasten the rubber tube 46, the rotating handle 44 moves to the distal end side, presses the moving cylinder body 43, and as shown in FIG. 13, the rubber tube 46 that is provided between the moving cylinder body 43 and the fixed ring member 41 is crushed, and extends in diameter to protrude in the outside diameter direction.

Thereby, the insertion portion guide tube 21 is fixed to the external access port OAP by the rubber tube 46 that is protruded in the outside diameter direction of the second fixing portion 24 contacting the hole portion inner circumferential wall in the thickness direction of the external access port OAP of the skin S in such a manner as to press the hole portion inner circumferential wall.

Second Embodiment

Next, a second embodiment of the present invention will be described hereinafter.

Here, another configuration of the second fixing portion of the first embodiment will be described.

Note that, concerning the same components as described in the first embodiment, the same reference signs are used, and the detailed description of the components will be omitted.

Figure 14:
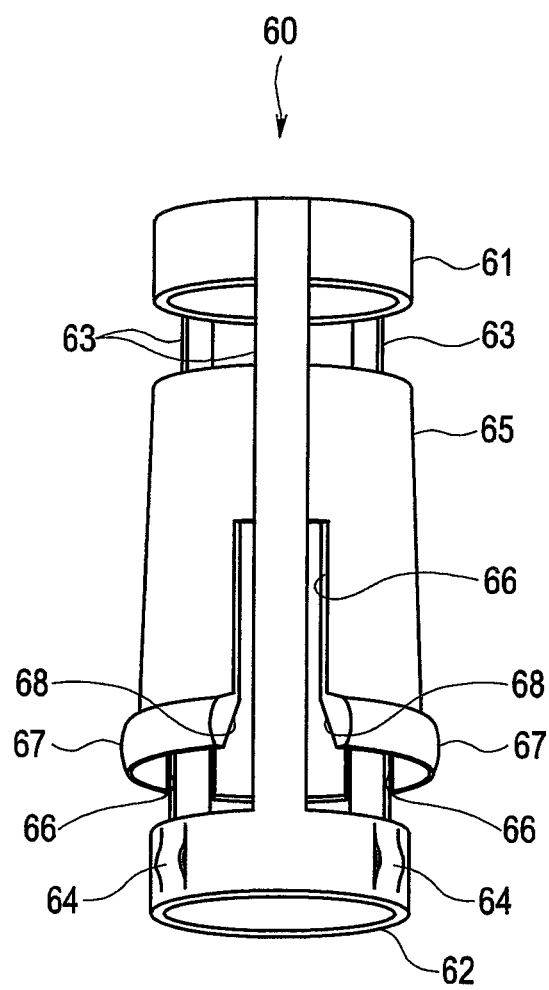
FIG. 14 is a perspective view showing a configuration of a second fixing portion according to a second embodiment of the present invention.
Figure 15:
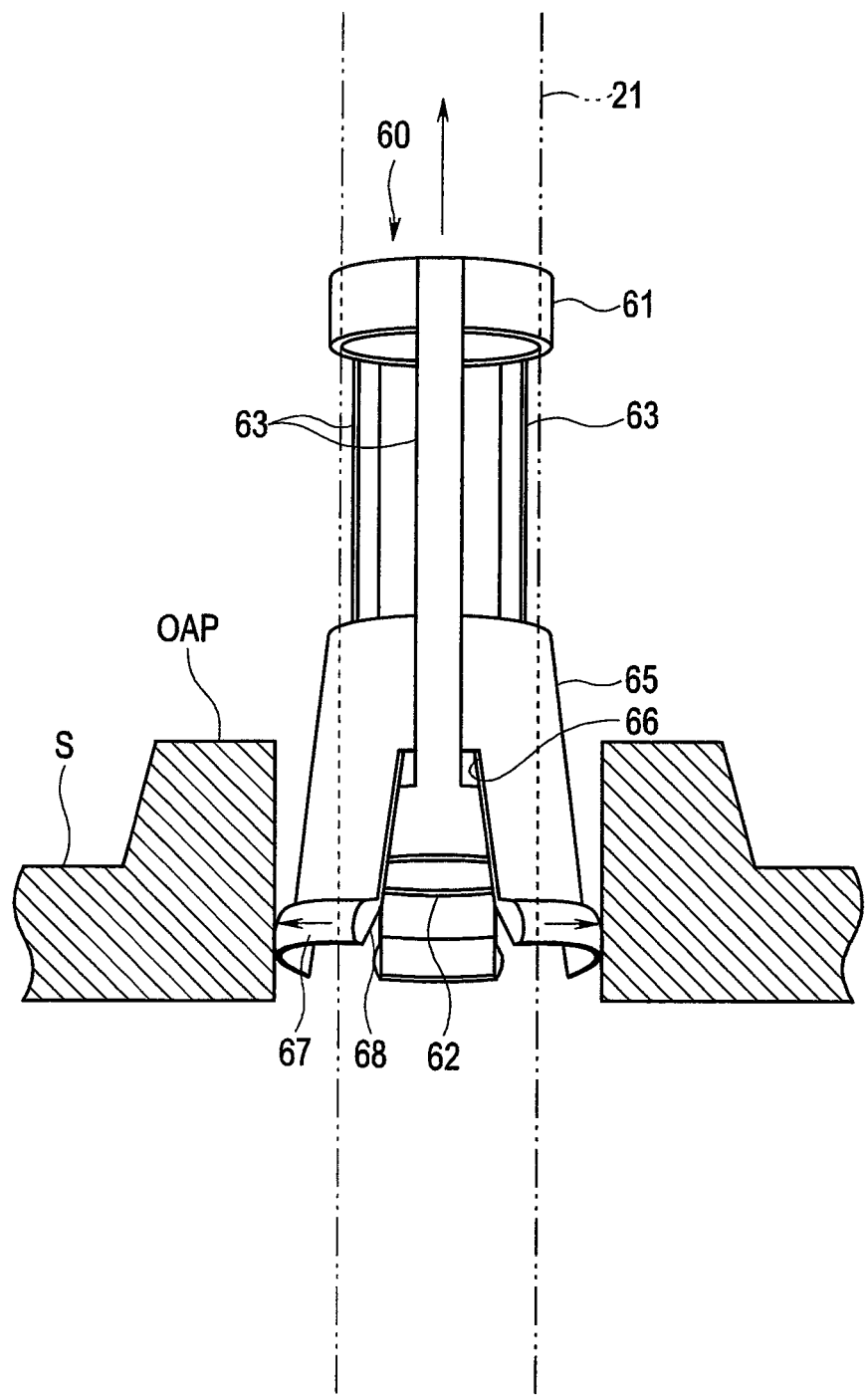
FIG. 15 is a partial sectional view showing a state in which the second fixing portion is inserted into the external access port, according to the second embodiment of the present invention.
Figure 16:
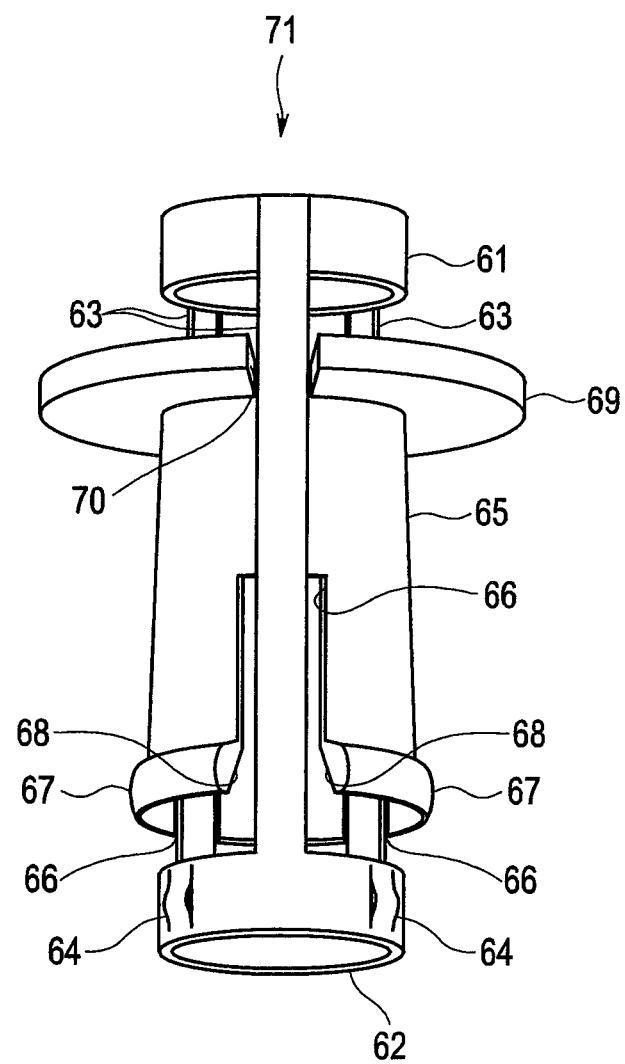
FIG. 16 is a perspective view showing a second fixing portion of a first modification, according to the second embodiment of the present invention.
Figure 17:
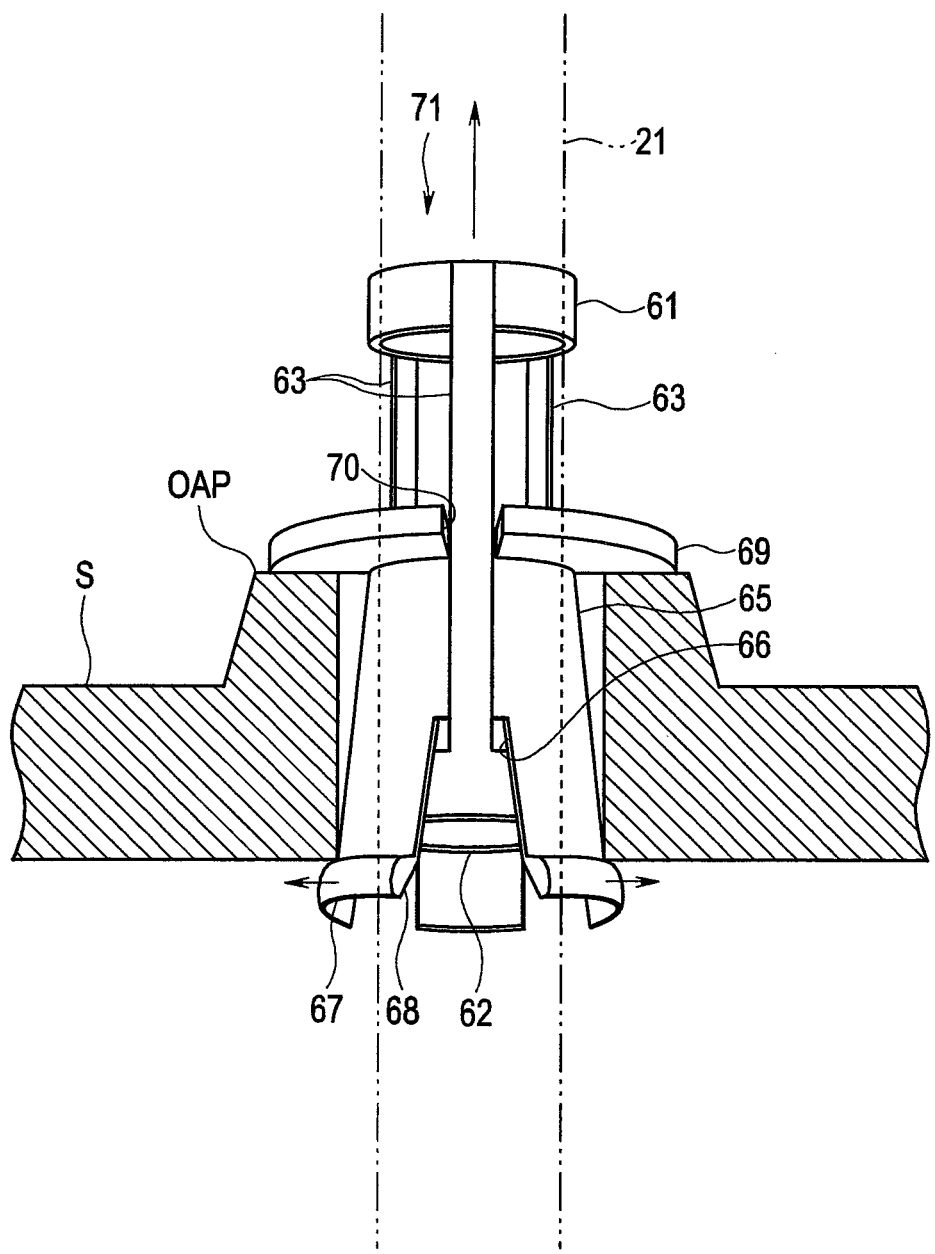
FIG. 17 is a partial sectional view showing a state in which the second fixing portion of the first modification is inserted into the external access port, according to the second embodiment of the present invention.
Figure 18:
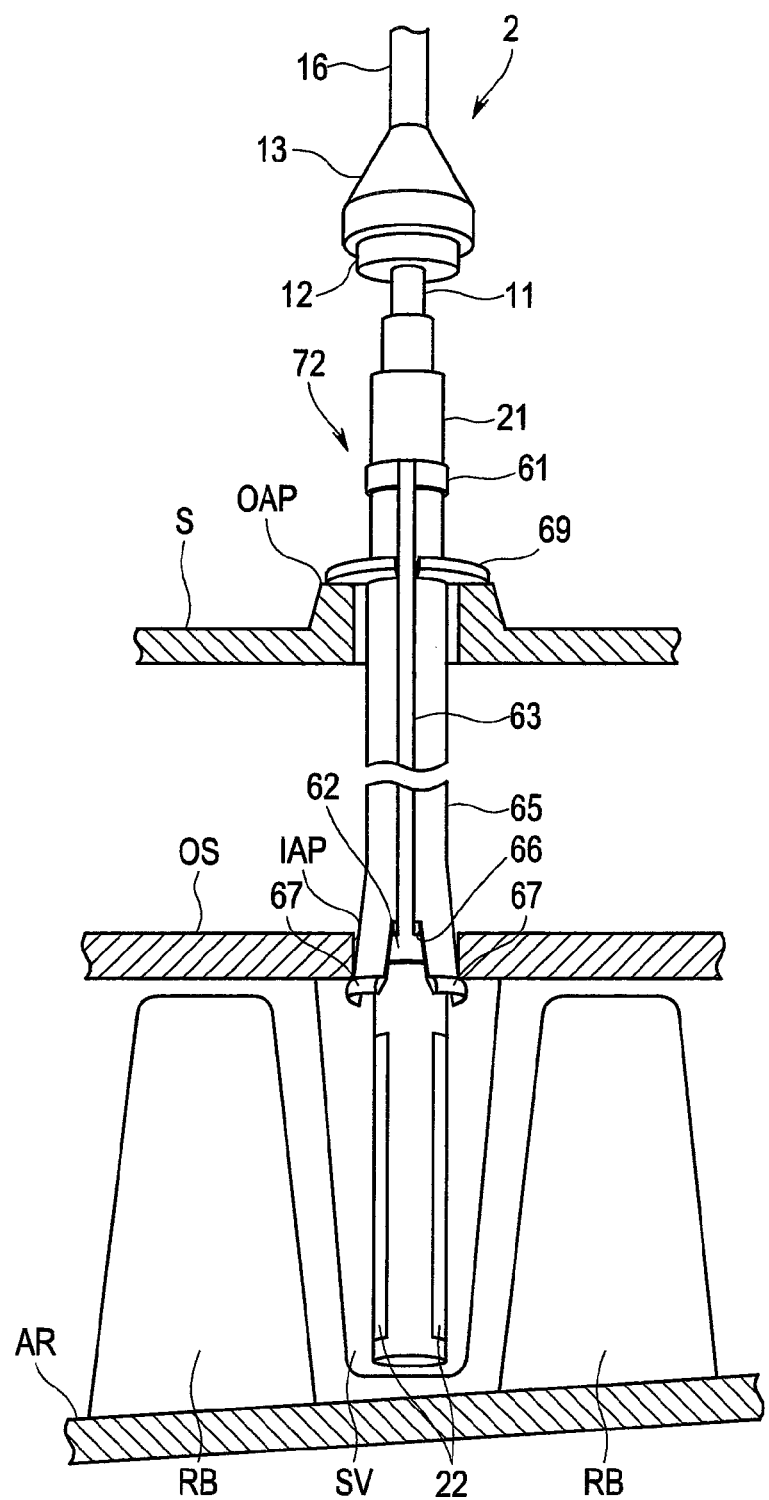
FIG. 18 is a partial sectional view showing a state of inspection of a high pressure compressor section of a second modification, according to the second embodiment of the present invention.
Figure 19:
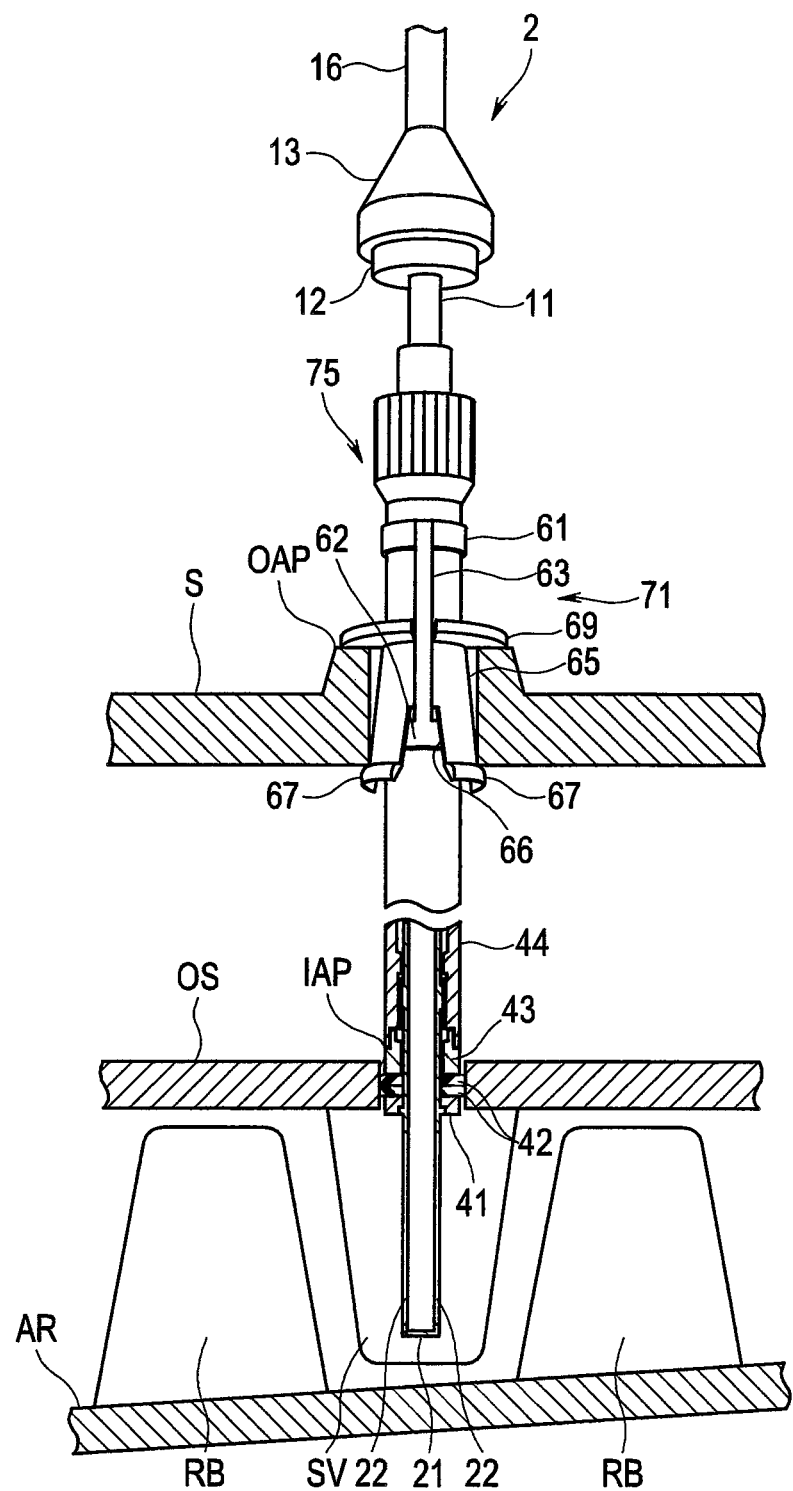
FIG. 19 is a partial sectional view showing a state of inspection of a high pressure compressor section of a third modification, according to the second embodiment of the present invention.

FIG. 14 to FIG. 19 relate to the second embodiment of the present invention. FIG. 14 is a perspective view showing a configuration of the second fixing portion. FIG. 15 is a partial sectional view showing a state in which the second fixing portion is inserted into the external access port. FIG. 16 is a perspective view showing a configuration of a second fixing portion of a first modification. FIG. 17 is a partial sectional view showing a state in which the second fixing portion of the first modification is inserted into the external access port. FIG. 18 is a partial sectional view showing a state of inspection of a high pressure compressor section of a second modification. FIG. 19 is a partial sectional view showing a state of inspection of a high pressure compressor section of a third modification.

As shown in FIG. 14, a second fixing portion 60 of the present embodiment is configured by having a first ring portion 61, a second ring portion 62 at which three arm portions 63 in this case that have end portions fixed to the first ring portion 61 are extensively provided equidistantly on a circumference thereof, and a fixing cylinder portion 65 that is placed between the first ring portion 61 and the second ring portion 62, and is placed to freely advance and retract in such a manner as to be fitted in an internal side of the three arm portions 63.

That is, in the second fixing portion 60, the first ring portion 61 is connected by the three arm portions 63 that are provided extensively from the second ring portion 62, and the fixing cylinder portion 65 is placed in an inside of the three arm portions 63.

In the second ring portion 62, three projected portions 64 in this case (only two are illustrated in FIG. 14) that are each deformed to protrude in an outside diameter direction along two notches are formed equidistantly on an outer circumferential portion.

In the fixing cylinder portion 65, three cutout portions 66 are formed from one end portion which is at the second ring portion 62 side to a midpoint portion are formed at positions along the respective arm portions 63. Further, in the fixing cylinder portion 65, a convex portion 67 that is projected in the outside diameter direction is formed on an outer circumferential portion of an end portion at the second ring portion 62 side. In the fixing cylinder portion 65, a taper 68 is formed to extend to a direction of one end portion at the second ring portion 62 side, at an inner surface side of the convex portion 67.

When the second fixing portion 60 that is configured as above is fixed to the external access port OAP of the skin S, the second fixing portion 60 is inserted into the hole portion of the external access port OAP, and is pulled in such a manner that the second ring portion 62 slides to be fitted into the fixing cylinder portion 65, and one end portion located at the second ring portion 62 side of the fixing cylinder portion 65 extends in diameter, as shown in FIG. 15.

More specifically, in the second fixing portion 60, the second ring portion 62 slides with the three arm portion 63 and is fitted into the fixing cylinder portion 65, when the first ring portion 61 is pulled. At this time, the second ring portion 62 smoothly advances into the fixing cylinder portion 65 by the taper 68 of the fixing cylinder portion 65, and the three projected portions 64 respectively abut on the inner circumferential face of the fixing cylinder portion 65. Subsequently, in the fixing cylinder portion 65, the respective projected portions 64 contact the inner circumferential face, whereby three end piece portions divided by the three cutout portions 66 extend in diameter in the outside diameter direction.

Thereby, as shown in FIG. 15, the second fixing portion 60 is fixed to the external access port OAP by the convex portions 67 that are formed on the three end piece portions extended in diameter of the fixing cylinder portion 65 contacting the hole portion inner circumferential wall in the thickness direction of the external access port OAP in such a manner as to press the hole portion inner circumferential wall.

Note that the second fixing portion 60 is configured to be substituted for the second fixing portion 24 of the first endoscope guide apparatus 3 or the second endoscope guide apparatus 4. When the second fixing portion 60 is substituted for the second fixing portion 24, the fixing cylinder portion 65 is brought into the state in which the fixing cylinder portion 65 is fixed to the insertion portion guide tube 21.

From the above description, the endoscope system 1 of the present embodiment can fix the insertion portion guide tube 21 of the first endoscope guide apparatus 3 or the second endoscope guide apparatus 4 so that the insertion portion guide tube 21 does not move without the axis swinging by fixing the insertion portion guide tube 21 at two spots of the second fixing portion 60, in addition to fixation of the insertion portion guide tube 21 to the engine E by the first fixing portion 23 or the fixing flange 25 as the first fixing portion.

Thereby, the endoscope system 1 of the present embodiment also can guide the insertion portion 11 of the borescope 2 in the state in which the insertion portion guide tube 21 of the first endoscope guide apparatus 3 or the second endoscope guide apparatus 4 is fixed so that the observation distance from the stator vane SV or the rotor blade RB that is the blade of the engine E is stably kept constant, similarly to the first embodiment, and therefore, reduction in measurement precision by the borescope 2 can be prevented.

(First Modification)

A second fixing portion 71 may be configured so that an outward flange 69 is formed at an end portion at the first ring portion 61 side, of the fixing cylinder portion 65 as shown in FIG. 16, and the second fixing portion 71 is fixed by holding an outer surface and an inner surface of a hole portion periphery of the external access port OAP provided in the skin S by the outward flange 69 and the three convex portions 67 of the fixing cylinder portion 65, as shown in FIG. 17. Note that in the outward flange 69 of the fixing cylinder portion 65, cutout portions 70 are formed at positions along the respective arm portions 63.

In the second fixing portion 71 of the present modification, when the first ring portion 61 is pulled, the second ring portion 62 slides with the three arm portions 63 and advances into the fixing cylinder portion 65, and the three end piece portions divided by the three cutout portions 66 extend in diameter in the outside diameter direction, similarly to the above description.

In the second fixing portion 71 in this case is fixed to the external access port OAP in such a manner that the outward flange 69 of the fixing cylinder portion 65 is butted to the outer surface of the hole portion periphery of the external access port OAP, the convex portions 67 that are formed on the three end piece portions that expand in diameter, of the fixing cylinder portion 65 are caught at the inner surface of the hole portion periphery of the external access port OAP, and the second fixing portion 71 holds the skin S in the thickness direction by the outward flange 69 and the three convex portions 67. Thereby, fixing strength of the second fixing portion 71 can be enhanced.

Note that the second fixing portion 71 in this case is also configured to be substituted for the second fixing portion 24 of the first endoscope guide apparatus 3 or the second endoscope guide apparatus 4. When the second fixing portion 71 is substituted for the second fixing portion 24, the fixing cylinder portion 65 is brought into the state in which the fixing cylinder portion 65 is fixed to the insertion portion guide tube 21.

By the configuration as above, the insertion portion guide tube 21 inserted in the engine E can be made immovable without the axis of the insertion portion guide tube 21 swinging by being fixed at the two spots that are the internal access port IAP formed in the inner shroud IS or the outer shroud OS and the external access port OAP of the skin S by the first fixing portion 23 or the fixing flange 25 as the first fixing portion, and the second fixing portion 71.

Accordingly, the insertion portion 11 of the borescope 2 can be guided in the state in which the insertion portion guide tube 21 is fixed so that the observation distance from the stator vane SV or the rotor blade RB that is the blade of the engine E is stably kept constant, and therefore, reduction in measurement precision by the borescope 2 can be prevented.

(Second Modification)

Further, as shown in FIG. 18, as a similar configuration to the second fixing portion 71 of the first modification, a fixing portion 72 may be configured to have the fixing cylinder portion 65 extended so that the outward flange 69 is caused to abut on the outer surface of the hole portion periphery of the external access port OAP, and the three convex portions 67 of the fixing cylinder portion 65 are caught at the inner surface side of the inner shroud IS of the hole portion periphery of the internal access port IAP.

That is, the fixing portion 72 of the present modification is fixed so as to hold an outer side of the external access port OAP that is formed in the skin S, and an inner side of the internal access port IAP that is formed in the outer shroud OS by the outward flange 69 and the three convex portions 67. When the configuration as above is adopted, fixing strength of the fixing portion 72 can be enhanced.

Note that the fixing portion 72 in this case is configured to be substituted for the first fixing portion 23 and the second fixing portion 24 of the first endoscope guide apparatus 3. Alternatively, the fixing portion 72 is configured to be substituted for the first fixing portion 25 and the second fixing portion 24 of the second endoscope guide apparatus 4. When the fixing portion 72 is substituted, the fixing cylinder portion 65 is in the state in which the fixing cylinder portion 65 is fixed to the insertion portion guide tube 21.

When the configuration as above is adopted, the insertion portion guide tube 21 that is inserted in the engine E is fixed at the two spots that are the external access port OAP of the skin S and the internal access port IAP that is formed in the outer shroud OS by the fixing portion 72, whereby the insertion portion guide tube 21 can be made immovable without the axis of the insertion portion guide tube 21 swinging.

Accordingly, the insertion portion 11 of the borescope 2 can be guided in the state in which the insertion portion guide tube 21 is fixed so that the observation distance from the stator vane SV or the rotor blade RB that is the blade of the engine E is stably kept constant, and therefore, reduction in measurement precision by the borescope 2 can be prevented.

(Third Modification)

Further, as shown in FIG. 19, the first endoscope guide apparatus 3 or the second endoscope guide apparatus 4 may be configured so that a first fixing portion 75 in this case is combined, that is of a similar configuration to the second fixing portion 24 described in the first embodiment, in addition to the second fixing portion 71 of the first modification.

More specifically, in the second fixing portion 71 in this case, the outward flange 69 of the fixing cylinder portion 65 is butted to the outer surface of the hole portion periphery of the external access port OAP, similarly to the aforementioned first modification. Subsequently, when the first ring portion 61 is pulled, the second ring portion 62 slides with the three arm portions 63, and advances into the fixing cylinder portion 65, and the three end piece portions divided by the three cutout portions 66 extend in diameter in the outside diameter direction. Thereby, the convex portions 67 that are formed on the three end piece portions that extend in diameter of the fixing cylinder portion 65 are caught at the inner surface of the hole portion periphery of the external access port OAP, and the second fixing portion 71 is fixed to the external access port OAP in such a manner as to hold the skin S in the thickness direction by the outward flange 69 and the three convex portions 67.

The first fixing portion 75 in this case is configured so that the length of the rotating handle 44 of the second fixing portion 24 of the first embodiment is extended, and the rotating handle 44 is rotatably inserted into the first ring portion 61 and the second ring portion 62 of the second fixing portion 71.

Note that since in the first fixing portion 75, the other components are the same as those of the second fixing portion 24, the same reference signs are used for the components, and the detailed description thereof will be omitted.

First, the first fixing portion 75 is inserted into a position where the two O-rings 42 face the hole portion inner circumferential wall in the wall thickness direction of the internal access port IAP of the outer shroud OS. When in the first fixing portion 75, the rotating handle 44 is rotationally operated to move to the distal end side from the above state, the rotating handle 44 presses the moving cylinder body 43 to the distal end side, and the two O-rings 42 provided between the moving cylinder body 43 and the fixed ring member 41 are crushed and protrude in the outside diameter direction.

Thereby, the two O-rings 42 contact the hole portion inner circumferential wall in the wall thickness direction of the internal access port IAP of the outer shroud OS in such a manner as to press the hole portion inner circumferential wall, and thereby the first fixing portion 75 is fixed to the internal access port IAP.

Note that the first fixing portion 75 and the second fixing portion 71 in this case are configured to be substituted for the first fixing portion 23 and the second fixing portion 24 of the first endoscope guide apparatus 3. Alternatively, the first fixing portion 75 and the second fixing portion 71 are configured to be substituted for the first fixing portion 25 and the second fixing portion 24 of the second endoscope guide apparatus 4. When the first fixing portion 75 and the second fixing portion 71 are substituted, the fixing cylinder portion 65 and the fixed ring member 41 are brought into the state in which the fixing cylinder portion 65 and the fixed ring member 41 are fixed to the insertion portion guide tube 21.

When the configuration as above is adopted, the insertion portion guide tube 21 inserted in the engine E is fixed at the two spots that are the internal access port IAP formed in the outer shroud OS and the external access port OAP of the skin S by the first fixing portion 75 and the second fixing portion 71, whereby the insertion portion guide tube 21 can be made immovable without the axis of the insertion portion guide tube 21 swinging.

Accordingly, the insertion portion guide tube 21 can guide the insertion portion 11 of the borescope 2 in the state in which the insertion portion guide tube 21 is fixed so that the observation distance from the stator vane SV or the rotor blade RB that is the blade of the engine E is stably kept constant, and therefore, reduction in the measurement precision by the borescope 2 can be prevented.

In the endoscope system 1 described above, the configuration in which the insertion portion guide tube 21 of the first endoscope guide apparatus 3 or the second endoscope guide apparatus 4 is fixed to the engine E by the various fixing portions so as not to move without the axis swinging, and the insertion portion 11 of the borescope 2 is inserted into the insertion portion guide tube 21 and is guided is shown as an example, but the endoscope system 1 is not limited thereto, and various fixing portions may be directly provided at the insertion portion 11 of the borescope 2.

The invention described in the aforementioned embodiments is not limited to the embodiments and the modifications, and various other modifications can be carried out within the range without departing from the gist of the invention in the stage of carrying out the invention. Furthermore, in the above described embodiments, the invention at the various stages is included, and various inventions can be extracted by appropriate combinations in the plurality of components that are disclosed.

What is claimed is:

1. An endoscope system for inspecting a plurality of blades that are periodically disposed at a periphery of a rotary shaft of a rotor of an engine and that rotate around the rotary shaft, the endoscope system comprising:
   an endoscope having an insertion portion provided with an observation optical system;
   a guide tube that is insertable into the engine, the endoscope being insertable into the guide tube;
   a first fixing portion that is provided at a first position of the guide tube, the guide tube being fixable in an inside of the engine by the first fixing portion;
   a second fixing portion that is provided at a second position of the guide tube, the second position being separated from the first position along a longitudinal direction of the guide tube by a first predetermined distance, and the guide tube being fixable to an outer jacketing cover of the engine by the second fixing portion; and
   an observation opening portion provided at a position along the longitudinal direction of the guide tube such that a blade from among the plurality of blades is observable by the endoscope through the observation opening portion in a state in which the endoscope is inserted into the guide tube and the guide tube is fixed in the inside of the engine by the first fixing portion and the second fixing portion.

2. The endoscope system according to claim 1, wherein the first fixing portion is configured to abut on a case of the engine.

3. The endoscope system according to claim 2, wherein the first fixing portion is configured to abut on a shroud at an inner side of the case of the engine on which a stator vane is provided.

4. The endoscope system according to claim 2, wherein the first fixing portion is configured to abut on a shroud at an outer side of the case of the engine on which a stator vane is provided.

5. The endoscope system according to claim 4, wherein the first fixing portion comprises a fixing flange.

6. The endoscope system according to claim 1, wherein the guide tube is fixable to an access port provided in the outer jacketing cover by the second fixing portion.

7. The endoscope system according to claim 6, wherein the second fixing portion comprises a fixing cylinder portion including a slidable ring portion, and the slidable ring portion is slidable to increase a size of a diameter of a convex portion of the slidable ring portion.

8. The endoscope system according to claim 6, wherein the second fixing portion comprises a fixing flange, a plurality of convex portions, and a slidable ring portion, and the second fixing portion is configured to abut an outer circumferential face and an inner circumferential face of a periphery of a hole portion of the access port.

9. The endoscope system according to claim 1, wherein:
   the first fixing portion comprises a fixing portion having a plurality of convex portions and a slidable ring portion;
   the second fixing portion comprises a fixing flange;
   the fixing flange of the second fixing portion is configured to abut on an outside of an access port provided in the outer jacketing cover; and
   the convex portions of the first fixing portion are configured to abut on an outer shroud of the case of the engine on which a stator vane is provided.

10. The endoscope system according to claim 1, wherein:
    the first fixing portion is configured to abut on an outer shroud of the case of the engine on which a stator vane is provided; and
    the second fixing portion comprises a fixing cylinder portion including a slidable ring portion, a size of a diameter of a convex portion of the slidable ring portion being increasable so as to fix the guide tube to an access port provided in the outer jacketing cover by the second fixing portion.

11. The endoscope system according to claim 1, wherein the guide tube, the first fixing portion, the second fixing portion, and the observation opening portion are coaxially arranged along a same central axis.

12. The endoscope system according to claim 1, wherein the observation opening portion is provided at a third position of the guide tube, the third position being separated from the first position along the longitudinal direction of the guide tube by a second predetermined distance, and the second predetermined distance being greater than the first predetermined distance.

13. The endoscope system according to claim 1, wherein the guide tube comprises a rigid tube.

* * * * *